(12) United States Patent
Fieselmann et al.

(10) Patent No.: US 10,028,715 B2
(45) Date of Patent: Jul. 24, 2018

(54) CREATING A VESSEL IMAGE AND FLUOROSCOPICALLY REPRESENTING VESSELS

(71) Applicants: Andreas Fieselmann, Erlangen (DE); Markus Kowarschik, Erlangen (DE); Wei Wei, Erlangen (DE)

(72) Inventors: Andreas Fieselmann, Erlangen (DE); Markus Kowarschik, Erlangen (DE); Wei Wei, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 108 days.

(21) Appl. No.: 14/811,522

(22) Filed: Jul. 28, 2015

(65) Prior Publication Data

US 2016/0022233 A1 Jan. 28, 2016

(30) Foreign Application Priority Data

Jul. 28, 2014 (DE) .................. 10 2014 214 772

(51) Int. Cl.
*G06K 9/00* (2006.01)
*A61B 6/00* (2006.01)
(Continued)

(52) U.S. Cl.
CPC .............. *A61B 6/481* (2013.01); *A61B 5/055* (2013.01); *A61B 5/489* (2013.01); *A61B 6/4441* (2013.01);
(Continued)

(58) Field of Classification Search
CPC . G06T 2207/10076; G06T 2207/30101; G06T 7/0081
See application file for complete search history.

(56) References Cited

U.S. PATENT DOCUMENTS 4,504,908 A * 3/1985 Riederer ................ A61B 6/481
128/922
4,536,790 A * 8/1985 Kruger ................ H04N 5/3205
348/E5.089
(Continued)

FOREIGN PATENT DOCUMENTS

DE    102007024450 A1    11/2008
WO    WO2014162273 A1    10/2014

OTHER PUBLICATIONS

B. Davis, K. Royalty, M. Kowarschik, C. Rohkohl, E. Oberstar, B. Aagaard-Kienitz, D. Niemann, O. Ozkan, C. Strother, and C. Mistretta, "4D Digital Subtraction Angiography: Implementation and Demonstartion of Feasibility." American Society of Neuroradiology 34, Seiten 1914-1921, 2013.
(Continued)

*Primary Examiner* — Gandhi Thirugnanam
(74) *Attorney, Agent, or Firm* — Lempia Summerfield Katz LLC

(57) ABSTRACT

A method for creating a selective vessel image within a volume section of an examination object using an imaging system is provided. The method includes creating a vessel image of the volume section. The creating of the vessel image includes acquiring imaging data of the volume section within a predetermined time interval using the imaging system, determining a maximum opacity within the time interval on account of a contrast agent administered to the examination object per pixel of the vessel image, and segmenting vessels. The segmenting includes deciding, depending on the maximum opacity of the pixel, whether the respective pixel belongs to the vessel. The method also includes determining a contrast agent arrival time per pixel of the vessel image, and segmenting whether the respective
(Continued)

vessel of the vessel image belongs to a vessel of the selective vessel image.

18 Claims, 4 Drawing Sheets

(51) Int. Cl.
  *A61B 5/055* (2006.01)
  *G06T 7/11* (2017.01)
  *A61B 5/00* (2006.01)
(52) U.S. Cl.
  CPC .............. *A61B 6/487* (2013.01); *A61B 6/504* (2013.01); *A61B 6/5217* (2013.01); *G06T 7/11* (2017.01); *A61B 5/0035* (2013.01); *G06T 2207/10076* (2013.01); *G06T 2207/20224* (2013.01); *G06T 2207/30101* (2013.01)

(56) References Cited

U.S. PATENT DOCUMENTS

| | | | | |
|---|---|---|---|---|
| 6,614,447 | B1* | 9/2003 | Bhatia | G06T 15/005 |
| | | | | 345/592 |
| 2001/0052906 | A1* | 12/2001 | Chen | G06T 11/00 |
| | | | | 345/629 |
| 2007/0225606 | A1* | 9/2007 | Naghavi | A61B 5/015 |
| | | | | 600/438 |
| 2009/0302840 | A1* | 12/2009 | Fung | G01R 33/4818 |
| | | | | 324/309 |
| 2011/0054295 | A1* | 3/2011 | Masumoto | A61B 5/055 |
| | | | | 600/407 |
| 2011/0230765 | A1* | 9/2011 | Guracar | A61B 8/06 |
| | | | | 600/458 |
| 2012/0093390 | A1* | 4/2012 | Wiemker | G06T 7/20 |
| | | | | 382/134 |
| 2013/0058555 | A1* | 3/2013 | Miao | G06K 9/6203 |
| | | | | 382/132 |
| 2013/0077839 | A1* | 3/2013 | Horz | G06T 11/001 |
| | | | | 382/130 |
| 2015/0150526 | A1* | 6/2015 | Ohishi | A61B 6/463 |
| | | | | 378/62 |
| 2016/0022233 | A1* | 1/2016 | Fieselmann | A61B 6/481 |
| | | | | 382/130 |
| 2016/0035103 | A1* | 2/2016 | Stawiaski | G06T 7/0081 |
| | | | | 382/130 |

OTHER PUBLICATIONS

C. Kiefer et al.: Theoretical and clinical aspects of TWIST based 4D time-resolved MR angiography, IFMBE Proceedings, vol. 25, issue II, pp. 466-469, ISSN 16800737, 2009.

Clinical Application of 3D/4D MR Angiography in Cardiovascular Diseases, J. Barkhausen u.a., Department of diagnostic and Interventional Radiology and Neuroradiology University Hospital Essen, Germany MAGNETOM, p. 61-66, 2007.

German Office Action for related German Application No. 10 2014 214 772.7, dated May 6, 2015, with English Translation.

* cited by examiner

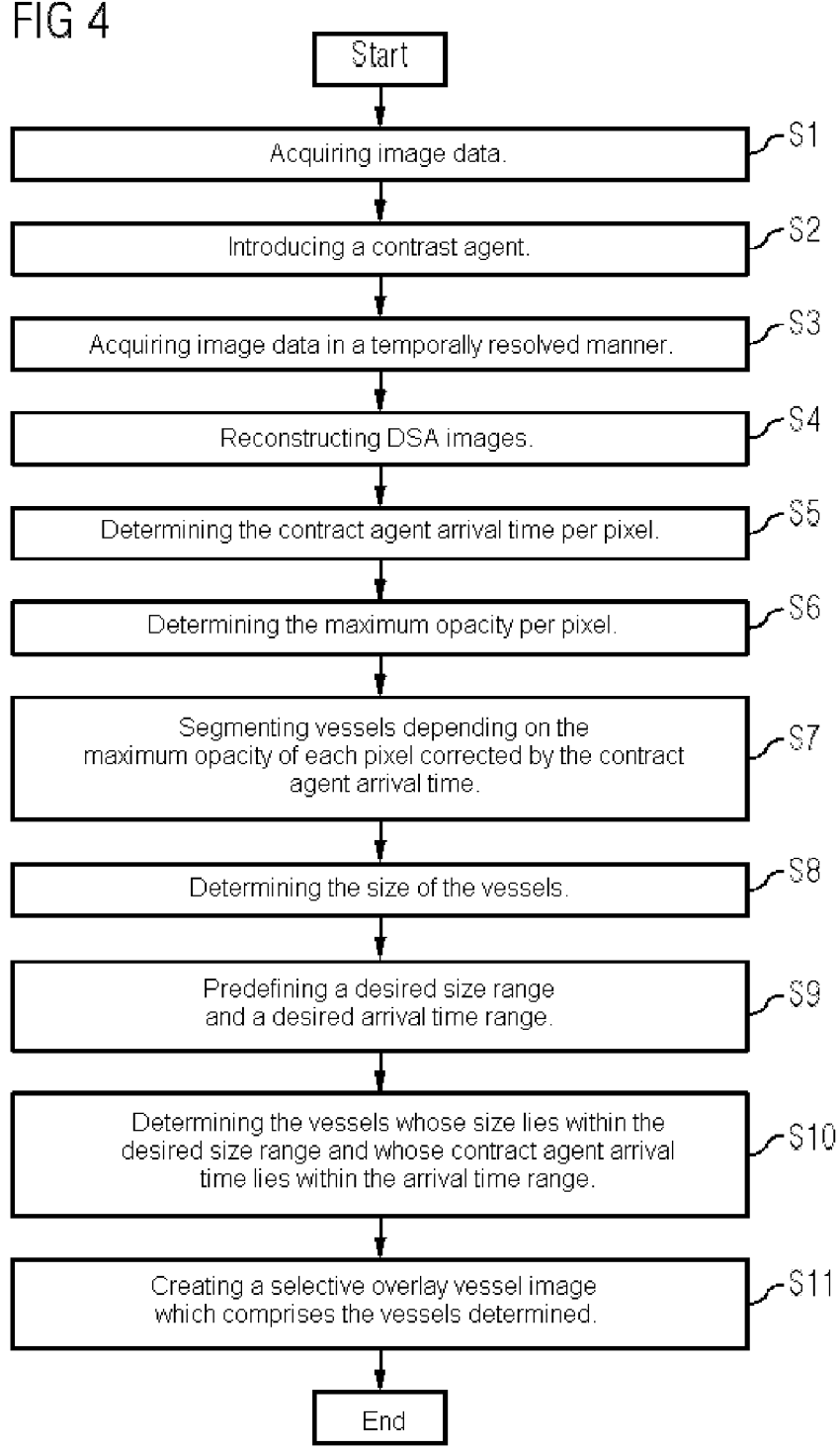

CREATING A VESSEL IMAGE AND FLUOROSCOPICALLY REPRESENTING VESSELS

This application claims the benefit of DE 10 2014 214 772.7, filed on Jul. 28, 2014, which is hereby incorporated by reference in its entirety.

BACKGROUND

The present embodiments relate to methods for creating vessel images, a method for fluoroscopically representing or fluoroscopically overlaying vessels, and the correspondingly designed imaging systems.

In vascular interventions (e.g., the insertion of a stent), the current fluoroscopic image is overlayed by an overlay vessel image in order, for example, to support the navigation of a catheter. This procedure is also known as "Roadmapping". In this case, the overlay vessel image is based on two-dimensional or three-dimensional vessel images.

SUMMARY AND DESCRIPTION

The scope of the present invention is defined solely by the appended claims and is not affected to any degree by the statements within this summary.

The roadmapping methods according to the prior art do not distinguish between different vessel types, and the overlay vessel image thus encompasses all types of sizes of vessels. In a specific vascular intervention, however, only the representation of specific vessels is used, and too much information may even disturb the work of the physician. When representing vessels with the aid of contrast agents, the problem exists that arterial vessels are represented comparatively to a more pronounced or greater degree than venous vessels, which is also a problem for the creation of overlay vessel images.

The present embodiments may obviate one or more of the drawbacks or limitations in the related art. For example, the problems known according to the prior art may be alleviated.

A method for creating a vessel image within a volume section of an examination object by an imaging system is provided. In this case, the method includes acquiring imaging data of the volume section within a predetermined time interval using the imaging system. The method includes determining a maximum opacity within the time interval. The maximum opacity is achieved by a contrast agent administered to the examination object for each pixel of the vessel image. In other words, the opacity is determined for each pixel in each image created from the imaging data in order to determine the maximum capacity within the predetermined time interval from the determined opacities per pixel. In the three-dimensional case (e.g., 3D+t modality (4D digital subtraction angiography or 4D magnetic resonance angiography)), the pixel corresponds to a voxel. The method also includes determining a contrast agent arrival time per pixel of the vessel image. The arrival time of the contrast agent in the case of a pixel may be defined, for example, by the point in time at which the opacity for the pixel proceeding from an opacity without a contrast agent has for the first time risen above a predetermined threshold value or reached the maximum. The method includes segmenting vessels by deciding, depending on the maximum opacity of the respective pixel and the contrast agent arrival time of the respective pixel, whether or not the respective pixel belongs to a vessel.

By carrying out the segmenting of the vessels not only based on the maximum opacity but also depending on the contrast agent arrival time, it is advantageously possible to counteract the effect that the opacity of a pixel under otherwise identical conditions is all the lower, the later the contrast agent reaches the respective pixel. This effect stems from the fact that the contrast agent becomes further diluted and thus has a lower concentration per unit volume, the longer the distance between the injection site, at which the contrast agent is injected, and the respective pixel.

In this case, the opacity may be determined relative to a specific path of a beam (e.g., x-ray beam) through the volume section based on a pixel value. In this case, the pixel value corresponds to the value of the pixel on the detector situated at the end of the beam path. By way of example, the opacity A may be determined based on the Lambert-Beer law (see equation (1)).

$$I = I_0 \times \exp(-A) \quad (1)$$

In this case, I corresponds to the pixel value, and $I_0$ denotes the intensity of the incident beam (e.g., without attenuation). In this case, the opacity A may also be interpreted as a line integral of an absorption coefficient or attenuation coefficient along the beam path through the volume section.

The images on the basis of which the maximum capacity and the contrast agent arrival time per pixel are determined are created, for example, by digital subtraction angiography. In this case, first images without previous contrast agent injection and second images after a previous contrast agent injection are created from the same volume section. The images created according to one or more of the present embodiments correspond, for example, to a subtraction of corresponding first and second images.

The segmenting of vessels depending on the maximum opacity and the contrast agent arrival time is carried out, for example, based on a corrected opacity that is calculated per pixel. In this case, the corrected opacity of the respective pixel is all the greater, the greater the maximum opacity of the pixel and the greater the contrast agent arrival time of the respective pixel. By way of example, the corrected opacity may be calculated based on a product of the maximum opacity of the respective pixel and a function value depending on the contrast agent arrival time of the respective pixel. In this case, the function by which the function value is calculated is a function that arises monotonically with the contrast agent arrival time. To put it another way, the corrected opacity $kOp(x,y,z)$ may be calculated by equation (2) below:

$$kOp(x,y,z) = MaxOp(x,y,z) \ast f(KAZ(x,y,z)) \quad (2)$$

In this case, $MaxOp(x,y,z)$ corresponds to the maximum opacity of the respective pixel at the location given by the coordinates x, y, z, $KAZ(x,y)$ is the contrast agent arrival time of the respective pixel, and $f(\ )$ is the monotonically rising function that is dependent on the contrast agent arrival time. While the coordinates x, y and z are required in the case of a three-dimensional vessel image, only the coordinates x and y are required for creating a two-dimensional vessel image. The z-coordinate would thus be omitted, for example, in equation (1) above.

The respective pixel belongs to a vessel of the vessel image to be created, for example, if the corrected opacity of the respective pixel is greater than a predetermined opacity threshold value.

By using the corrected opacity during the segmenting, the above-described dilution effects of the contrast agent may be compensated for.

In accordance with one embodiment, even further pixels may be assigned to a vessel. The further pixels would not belong to a vessel as a result of the above-described segmenting. For this purpose, in accordance with this embodiment, the maximum total opacity is determined for vessel pixels (e.g., pixels that belong to a vessel according to the segmenting) of the same vessel that are arranged on the same straight line perpendicular to the flow direction of the vessel. In other words, for the vessel pixels lying on the straight line, the maximum of the maximum opacities of the vessel pixels is determined. A pixel that lies on the straight line adjacent to a vessel pixel is likewise classified as a vessel pixel according to the segmenting if the maximum opacity of the pixel is greater than a product of the previously calculated maximum total opacity and a predefined percentage.

By this procedure, precisely in the case of large vessels, pixels within the vessel edges of the respective vessels are also classified as vessel pixels, such that the full extent of the vessel is acquired.

In accordance with a further embodiment, a segmented vessel (e.g., smaller vessel) having two vessel edges that are likewise vessel edges of two different segmented vessels (e.g., larger vessels) is eliminated from the vessel image to be created, such that the vessel pixels belonging to the vessel (e.g., smaller vessel) are classified as no longer belonging to a vessel (e.g., no longer as vessel pixels). In this case, a vessel may be classified as a smaller vessel, for example, if the distance between the two edges of the vessel running substantially parallel lies below a predetermined distance threshold value.

This further embodiment makes it possible to subsequently correct an erroneous segmenting in image regions with a plurality distance (e.g., larger).

The imaging data is acquired, for example, by a temporally resolved two-dimensional or a temporally resolved three-dimensional data acquisition. The vessel image may be two-dimensional or three-dimensional. In this case, a temporally resolved two-dimensional data acquisition is understood to be, for example, a 2D+t DSA (e.g., digital subtraction angiography), where "2D" stands for two-dimensional, and "+t" stands for temporally resolved. A temporally resolved data acquisition provides that pixel values are present per image pixel at different points in time. In this case, the temporal resolution depends on the imaging method and on the spatial resolution. Besides two-dimensional methods, three-dimensional methods known as 3D+t DSA or 4D DSA may also be used.

The realization of a 4D DSA using a permanently installed C-arm is described, for example, in "4D Digital Subtraction Angiography: Implementation and Demonstration of Feasibility," AJNR Am J Neuroradial 2013 34, pages 1914-1921. In this case, approximately 30 recordings per second are carried out, and approximately half a rotation of the C-arm is performed, for example, within 5 s. However, other acquisition protocols using a C-arm may also be provided (e.g., a scan of a larger angular interval).

As illustrated, for example, in "Clinical Application of 3D/4D MR Angiography in Cardiovascular Diseases," J. Barkhausen et al., MAGNETOM Flash 2/2007, with a magnetic resonance installation, for example, with the use of the sequence TWIST ("Time-resolved With Stochastic Trajectories"), a temporal resolution of 1 to 5 seconds may be achieved depending on the sequence parameters and the spatial resolution. A temporal resolution of below 1 second may even be provided with the use of parallel measurement techniques.

Other sequences that enable a high temporal resolution during MR measurements are k-t SENSE, UNFOLD-SENSE, Noquist, k-t GRAPPA, 3D-TRICKS, TREAT, which may be gathered from "Theoretical and clinical aspects of TWIST based 4D time-resolved MR angiography," DOI:10.1007/978-3-642-03879-2_131.

The imaging system may include an x-ray system, a magnetic resonance installation, or a computed tomography system. Combinations of a plurality of these devices may also be provided.

While the creation of a normal two-dimensional x-ray image does not require any reconstruction, a reconstruction of the image on the imaging data is provided if volume data (e.g., three-dimensional images) is to be generated. The imaging data for generating volume data may be acquired by a magnetic resonance installation, a computed tomography system, or an x-ray C-arm system.

The segmenting of the vessels may also be carried out depending on morphological information of the examination object (e.g., depending on prior knowledge about the structure of the vessel tree of the examination object).

In the context of one or more of the present embodiments, a method for creating a selective vessel image within a volume selection of an examination object with the aid of an imaging system is also provided. In this case, the method includes creating a vessel image of the volume section. In this case, creating the vessel image includes the following subsets: acquiring imaging data of the volume section within a predetermined time interval by the imaging system; determining a maximum opacity within the time interval on account of a contrast agent administered to the examination object per pixel or of the vessel image; segmenting vessels by deciding, depending on the maximum opacity of the respective pixel, whether or not the respective pixel belongs to a vessel; determining a start per pixel of the vessel image; and segmenting whether the respective pixel of the vessel image also belongs to a vessel of the selective vessel image. For the segmenting, an area of the respective vessel that is flowed through perpendicular to the flow direction within the respective vessel is estimated. If this area that is flowed through is less than a predetermined maximum size threshold value and greater than a predetermined minimum size threshold value and if simultaneously the contrast agent arrival time (e.g., average contrast agent arrival time) of the pixels of the vessel is less than a predefined maximum contrast agent arrival time threshold value and greater than a predefined minimum contrast agent arrival time threshold value, then the respective vessel belongs to the vessels of the selective vessel image.

The method according to one or more of the present embodiments for creating a selective vessel image accordingly creates the selective vessel image depending on the opacity caused with the aid of the contrast agent, and depending on the arrival time at which the contrast agent arrives in the respective vessel. In this case, for example, a physician may predefine a window for the vessel size (e.g., defined by the minimum and maximum size threshold values) and a window for the contrast agent arrival time (e.g., defined by the minimum and maximum contrast agent arrival time threshold values). From the vessel image (e.g., provisional vessel image) created purely from the maximum opacity, only those vessels that lie within the two defined windows are accepted into the selective vessel image.

The selective vessel image according to one or more of the present embodiments thus contains only the desired vascular information or vessel information.

In accordance with one embodiment, the above-described method for creating a vessel image is used for creating the provisional vessel image.

In this embodiment, accordingly, the contrast agent arrival time is also used for creating the provisional vessel image in order to correspondingly correct (e.g., increase) the opacity for the pixels for which the contrast agent arrival time has comparatively longer times.

In the two-dimensional case, the area of the respective vessel that is flowed through may be determined based on the length of a path that is perpendicular to a flow direction of the respective vessel and the ends of which correspond to the opposite edges of the vessel. For this purpose, the flow direction of the respective vessel may substantially lie within the plane of the two-dimensional vessel image in which the path to be measured also lies for determining the area that is flowed through.

In the context of one or more of the present embodiments, a method for fluoroscopically representing vessels with a volume section of an examination object using an imaging system, for example, for carrying out an intervention in a vessel system of the examination object is also provided. In this case, a current image (e.g., a live image) of the volume section is overlaid by a selective vessel image created according to one or more of the present embodiments. In this case, the selective vessel image is created by one of the above-described methods according to one or more of the present embodiments for creating a selective vessel image.

On account of the creation of the selective vessel image, which is overlaid on the current image, such that only the vessels that correspond to the vessels of the selective vessel image are visible in the current image, according to one or more of the present embodiments, the medical practitioner viewing the current image is advantageously not distracted by irrelevant vessel information. In other words, through the choice of the corresponding threshold values, the medical practitioner has the option of predefining purposefully or selectively what vessel information the medical practitioner would like to see in the current image or live image. By way of example, only the vessels with a contrast agent arrival time that is within a specific time period and with thickness or dimensions that likewise are within a specific range, which are defined by the corresponding threshold values, may be visible in the live image.

An imaging system that is configured for creating a vessel image within a volume section of an examination object is also provided. In this case, the imaging system is also configured to: acquire imaging data of the volume section within a predefined time interval; determine, from images created from the imaging data, a maximum opacity within the predetermined time interval depending on a contrast agent injected into the imaging system per pixel of the vessel image; determine the contrast agent arrival time per pixel of the vessel image; and segment vessels of the vessel image by the system deciding, depending on the maximum opacity of the pixel and the contrast agent arrival time of the pixel, whether or not the respective pixel belongs to a vessel of the vessel image.

The advantages of the imaging system substantially correspond to the advantages of the method for creating a vessel image, which have been explained in detail above and will not be repeated here.

A further imaging system is also provided. The further imaging system is configured to create a selective vessel image with a volume section of an examination object. In this case, the further imaging system is also configured to create a vessel image of the volume section by the imaging system acquiring imaging data of the volume section within a predetermined time interval, determining a maximum opacity within the time interval depending on a contrast agent injected into the examination object per pixel of the vessel image, and segmenting vessels by the imaging system deciding, depending on the maximum opacity of the pixel, whether or not the respective pixel belongs to a vessel of the vessel image.

The imaging system is also configured to determine a contrast agent arrival time per pixel of the vessel image. The imaging system is configured to segment whether the respective vessel of the vessel image also belongs to a vessel of the selective vessel image by deciding that the vessel also belongs to a vessel of the selective vessel image only if an area of the vessel that is flowed through perpendicular to the flow direction within the vessel is less than a predetermined maximum size threshold value and greater than a predetermined minimum size threshold value, and if simultaneously the contrast agent arrival time (e.g., average arrival time) of the pixels of the vessel is less than a predefined maximum contrast agent arrival time threshold value and greater than a predefined minimum contrast agent arrival time threshold value.

In this case, too, the advantages of the further imaging system substantially correspond to the advantages of the method for creating a selective vessel image, which have been explained in detail above and will not be repeated here.

One or more of the present embodiments describe a computer program product (e.g., a computer program or software) that may be loaded into a memory (e.g., a non-transitory computer-readable storage medium) of a programmable controller or of a computing unit of an imaging system. With this computer program product, all or various above-described embodiments of the methods may be implemented if the computer program product runs in the controller or control device of the imaging system. In this case, the computer program product may use, for example, libraries and auxiliary functions to realize the corresponding embodiments of the methods. In other words, a claim directed to the computer program product is intended to afford protection, for example, for a computer program or software with which one of the above-described embodiments of the method may be implemented or which implements this embodiment. In this case, the software may be source code (e.g., C++) that is still to be compiled (e.g., translated) and linked, and for which is only to be interpreted, or executable software code that, for execution, only is to be loaded into the corresponding computing unit or control device.

The present embodiments disclose an electronically readable data carrier (e.g., a DVD, a magnetic tape or a USB stick), on which electronically readable control information items (e.g., software) are stored. If the control information items (e.g., software) are read from the data carrier and stored in a control device or computing unit of an imaging system, all embodiments of the method described above may be carried out.

The present embodiments may be carried out by an x-ray system having a mobile C-arm, and by an x-ray system having a stationary C-arm. The present embodiments may be used both for two-dimensional visualization and for three-dimensional visualization.

While according to the prior art the arrival time of the contrast agent or contrast agent bolus is not taken into account in the creation of an overlay vessel image, in the present embodiments, the arrival time is used for correcting the opacity and for selecting between different vessels to be represented. While according to the prior art in roadmapping solutions no distinction is drawn between different vessel types or vessel sizes and thus all vessels are represented, according to one or more of the present embodiments, only the vessels classified as important by the respective medical practitioner are imaged, and so the representation of disturbing information is avoided.

BRIEF DESCRIPTION OF THE DRAWINGS

FIG. 4 illustrates a flow chart for one embodiment of creating a selective vessel image.

DETAILED DESCRIPTION

Figure 1:
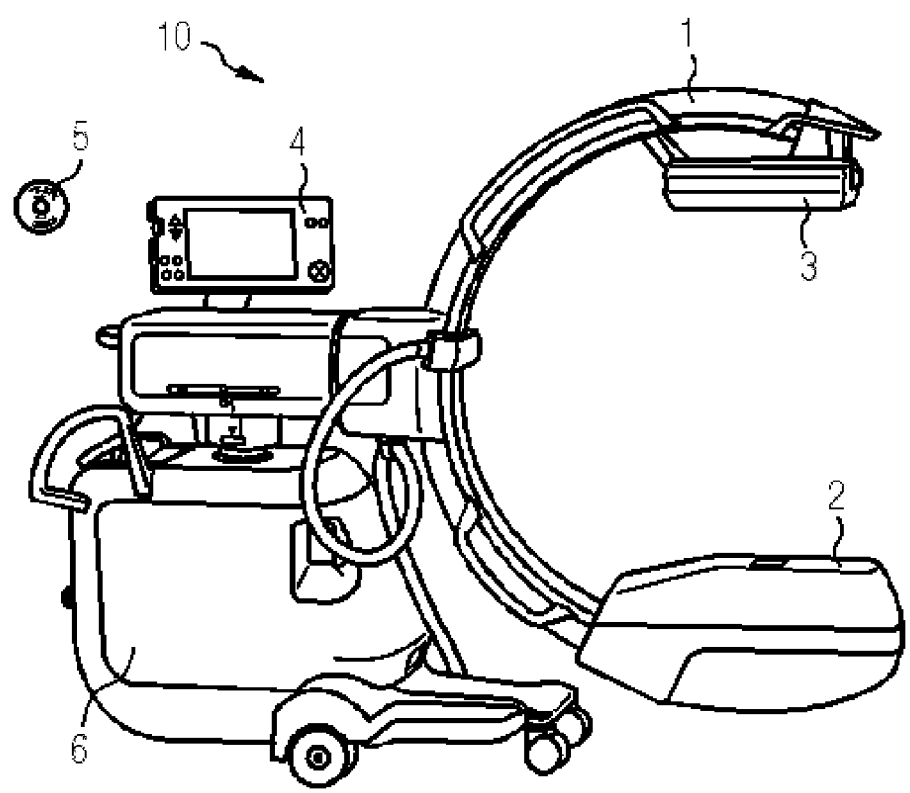
FIG. 1 shows one embodiment of an imaging system.

FIG. 1 illustrates one embodiment of a mobile x-ray system 10 including a control device 6, a C-arm 1 and a screen 4. The C-arm 1 includes an x-ray source 2 and a detector 3. In order to acquire imaging data of an examination object, the C-arm 1 generally remains stationary with respect to the examination object when creating two-dimensional information, while the C-arm 1 rotates around the examination object when creating three-dimensional information.

FIG. 1 illustrates one embodiment of a data carrier 5 that has stored a computer program product according to one or more of the present embodiments (e.g., software).

Figure 2:
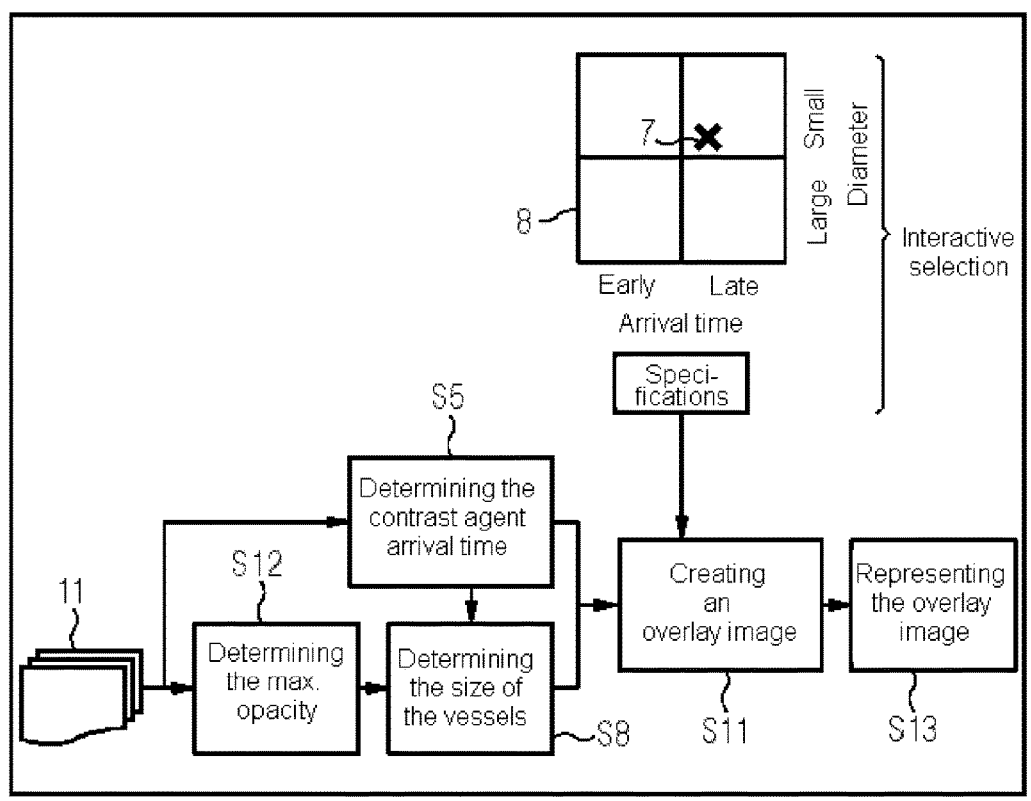
FIG. 2 illustrates one embodiment of a procedure for creating an overlay image.

FIG. 2 illustrates one embodiment of a procedure for creating a selective vessel image. DSA images that are created according to one or more of the present embodiments are present at the beginning of this procedure. Act S12 involves determining the maximum opacity in the DSA images. In parallel therewith, the contrast agent arrival time is determined in act S5. Based on the maximum opacity and the contrast agent arrival time, the extent of the vessels that are present in the DSA images is determined in act S8.

In the form of an interactive selection, an operator (e.g., the treating physician) may place a marking 7. The marking defines a range of a diameter size and a range of the contrast agent arrival time. Based on this predefinition or definition, depending on the contrast agent arrival time determined in act S5 and depending on the size of the respective vessels determined in act S8, a selective vessel image or overlay image is created in act S11. The selective vessel image contains only the vessels with size or diameter that lies in the predefined range of the diameter size and with a contrast agent arrival time that lies in the predefined range of the contrast agent arrival time. Act S13 involves representing the previously created selective image as overlay image together with a fluoroscopic live image.

Figure 3:
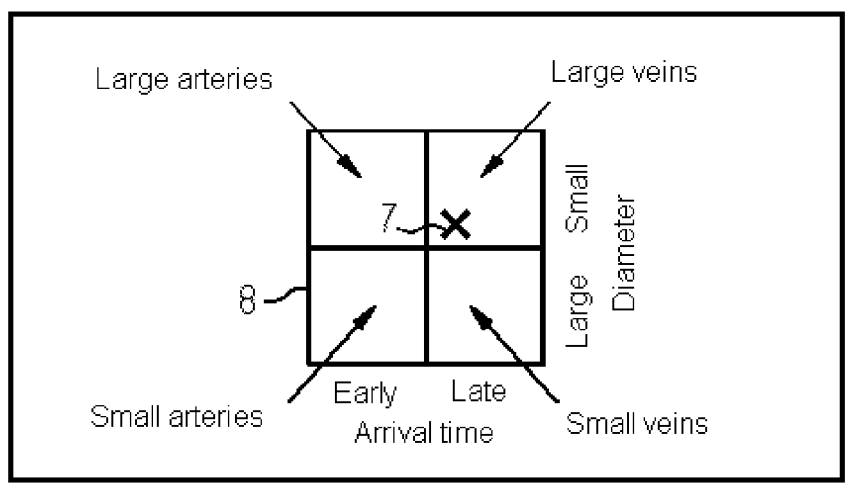
FIG. 3 illustrates a portion of FIG. 2 in detail.

The range 8 illustrated in FIG. 2 is illustrated in an enlarged view and in a manner provided with comments in FIG. 3. The range 8 representing a square is itself again divided into four equally sized squares or quadrants. If the range 8 is subdivided in equal halves into a range of early contrast agent arrival time and a range of late contrast agent arrival time, and in equal halves into a range of vessels having a large diameter and having a small diameter, then placing the marking 7 in the top left quadrant provides that only large arteries are represented in the selected vessel image, in the top right quadrant provides that only large veins are represented in the selective vessel image, in the bottom left quadrant provides that only small arteries are represented in the selective vessel image, and in the bottom right quadrant provides that only small veins are represented in the selective vessel image.

The marking 7 may also be placed such that the marking 7 lies in two or more quadrants. Placing a plurality of markings may also be provided, such that, for example, both large arteries and large veins are represented in the overlay vessel image and thus on the masked live vessel image.

FIG. 4 illustrates a flow chart for the creation, according to one or more of the present embodiments, of a selective vessel image.

Act S1 involves acquiring image data from a predetermined volume section of an examination object with the aid of an imaging system (e.g., a magnetic resonance installation or an x-ray system), without a contrast agent being injected into the examination object beforehand. Act S2 involves injecting a contrast agent into the examination object, and act S3 involves acquiring temporally resolved image data from the predetermined volume section with the aid of the imaging system. Therefore, while in act S1 it suffices to acquire image data in order to create or reconstruct a two-dimensional image or a three-dimensional image therefrom, in act S3, image data is acquired over a longer period of time (e.g., while the contrast agent is propagating in the examination object) in order to be able to track in the images the propagation of the contrast agent, for example, based on the opacity.

From the image data acquired in acts S1 and S3, DSA images are reconstructed or created in act S4 by an image information item with contrast agent being subtracted from an image information item without contrast agent per time step. Based on the DSA images, the contrast agent arrival time per pixel is created in S5, and the maximum opacity of each pixel is created in act S6.

Depending on the maximum opacity, which is corrected based on the contrast agent arrival time, vessels are segmented in act S7. For this purpose, based on the corrected maximum opacity of each pixel, for each pixel, a decision is made as to whether or not this pixel is a vessel pixel. The segmented vessels are then formed by vessel pixels.

Act S8 involves determining the size of the vessels segmented in act S7.

Act S9 involves predefining a desired size range and a desired arrival time range. In this case, the desired size range is defined based on a lower size threshold value and an upper size threshold value, and the desired arrival time range is defined based on a lower contrast agent arrival time threshold value and an upper contrast agent arrival time threshold value.

Act S10 involves determining the vessels with a size that lies within the desired size range and with a contrast agent arrival time that lies within the arrival time range. Only the vessels determined in act S10 form the vessels present in the selective vessel image. Act S11 involves representing the selective vessel image as an overlay vessel image.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for creating a vessel image with a volume section of an examination object using an imaging system, the method comprising:
   acquiring imaging data of the volume section within a predetermined time interval;
   determining a maximum opacity within the predetermined time interval on account of a contrast agent administered to the examination object, the determining being per pixel of the vessel image, wherein opacity represents a concentration of contrast agent per unit volume;
   determining a contrast agent arrival time per pixel of the vessel image;
   calculating a corrected opacity for each pixel of the vessel image based on the maximum opacity and the contrast agent arrival time for the respective pixel; and
   segmenting vessels, the segmenting comprising deciding, depending on the calculated corrected opacity for the respective pixel, that the respective pixel belongs to a vessel.

2. The method of claim 1, wherein the respective pixel belongs to a vessel when the corrected opacity of the pixel is greater than a predetermined opacity threshold value, and
   wherein the greater the corrected opacity of the pixel is, the greater the maximum opacity of the pixel and the contrast agent arrival time of the pixel are.

3. The method of claim 1, wherein the respective pixel belongs to a vessel when the corrected opacity of the pixel is greater than a predetermined opacity threshold value, and
   wherein the corrected opacity is dependent on a product of the maximum opacity of the pixel and a function value dependent on the contrast agent arrival time of the pixel, when the function for calculating the function value rises monotonically with the contrast agent arrival time.

4. The method of claim 1, wherein the maximum total opacity is determined for vessel pixels of a vessel which are arranged on the same straight line perpendicular to the flow direction of the vessel,
   wherein a vessel pixel defines a pixel which belongs to a segmented vessel, and
   wherein a pixel that lies on the straight line adjacent to a vessel pixel is likewise segmented as a vessel pixel when a maximum opacity of the pixel is greater than a product of the maximum total opacity and a predefined percentage.

5. The method of claim 1, further comprising eliminating a segmented smaller vessel having two edges that are edges of two different segmented larger vessels from the vessel image to be created, such that the pixels of the smaller vessel no longer belong to a vessel.

6. The method of claim 1, wherein acquiring the imaging data comprises acquiring the imaging data using a temporally resolved two-dimensional or temporally resolved three-dimensional data acquisition, the vessel image is two-dimensional or three-dimensional, or a combination thereof.

7. The method of claim 1, further comprising reconstructing images depending on the acquired imaging data.

8. The method of claim 1, wherein the imaging system comprises an x-ray system, a magnetic resonance installation, a computed tomography system, or any combination thereof.

9. The method of claim 1, wherein the segmenting is carried out depending on morphological information of the examination object.

10. A method for creating a selective vessel image within a volume section of an examination object using an imaging system, wherein a vessel of the volume section is represented or suppressed in the selective vessel image selectively in a manner dependent on at least one predetermined criterion, the method comprising:
    creating a vessel image of the volume section, the creating comprising:
       acquiring imaging data of the volume section within a predetermined time interval using the imaging system;
       determining a maximum opacity within the predetermined time interval on account of a contrast agent administered to the examination object, the determining being per pixel of the vessel image; and
       segmenting vessels, the segmenting comprising deciding, depending on the maximum opacity of the pixel, whether the respective pixel belongs to the vessel;
    determining a contrast agent arrival time per pixel of the vessel image; and
    segmenting whether the respective vessel of the vessel image belongs to a vessel of the selective vessel image when an area of the vessel that is flowed through perpendicularly to a flow direction is smaller than a predetermined maximum size threshold value and larger than a predetermined minimum size threshold value, and when the contrast agent arrival time of the pixels of the vessel is less than a predefined maximum threshold value and greater than a predefined minimum contrast agent arrival time threshold value.

11. A method for creating a selective vessel image within a volume section of an examination object using an imaging system, wherein a vessel of the volume section is represented or suppressed in the selective vessel image selectively in a manner dependent on at least one predetermined criterion, the method comprising:
    creating a vessel image of the volume section, the creating comprising:
       acquiring imaging data of the volume section within a predetermined time interval;
       determining a maximum opacity within the predetermined time interval on account of a contrast agent administered to the examination object, the determining being per pixel of the vessel image;
       determining a contrast agent arrival time per pixel of the vessel image; and
       segmenting vessels, the segmenting comprising deciding, depending on the maximum opacity of the pixel and the contrast agent arrival time of the pixel, the respective pixel belongs to a vessel; and
    segmenting whether the respective vessel of the vessel image belongs to a vessel of the selective vessel image when an area of the vessel that is flowed through perpendicularly to a flow direction is smaller than a predetermined maximum size threshold value and larger than a predetermined minimum size threshold value, and when the contrast agent arrival time of the pixels of the vessel is less than a predefined maximum threshold value and greater than a predefined minimum contrast agent arrival time threshold value.

12. The method of claim 11, wherein the vessel image is two-dimensional,
wherein the flow direction of the respective vessel lies within a plane of the vessel image, and
wherein the area that is flowed through is determined based on a length of a path that is perpendicular to a flow direction of the respective vessel and is delimited by opposite edges of the vessel.

13. A method for fluoroscopically representing vessels within a volume section of an examination object using an imaging system, the method comprising:
creating a selective vessel image within the volume section of the examination object using the imaging system, wherein a vessel of the volume section is represented or suppressed in the selective vessel image selectively in a manner dependent on at least one predetermined criterion, the creating of the selective vessel image comprising:
creating a vessel image of the volume section, the creating of the vessel image comprising:
acquiring imaging data of the volume section within a predetermined time interval using the imaging system;
determining a maximum opacity within the predetermined time interval on account of a contrast agent administered to the examination object, the determining being per pixel of the vessel image; and
segmenting vessels, the segmenting comprising deciding, depending on the maximum opacity of the pixel, whether the respective pixel belongs to the vessel;
determining a contrast agent arrival time per pixel of the vessel image;
segmenting whether the respective vessel of the vessel image belongs to a vessel of the selective vessel image when an area of the vessel that is flowed through perpendicularly to a flow direction is smaller than a predetermined maximum size threshold value and larger than a predetermined minimum size threshold value, and when the contrast agent arrival time of the pixels of the vessel is less than a predefined maximum threshold value and greater than a predefined minimum contrast agent arrival time threshold value; and
overlaying a current image of the volume section with the selective vessel image.

14. An imaging system configured to create a vessel image within a volume section of an examination object, wherein the imaging system comprises:
an imaging device configured to acquire imaging data of the volume section within a predetermined time interval; and
a processor configured to:
determine, per pixel of the vessel image, a maximum opacity within the predetermined time interval on account of a contrast agent administered to the examination object, wherein opacity represents a concentration of contrast agent per unit volume;
determine a contrast agent arrival time per pixel of the vessel image;
calculate a corrected opacity for each pixel of the vessel image based on the maximum opacity and the contrast agent arrival time for the respective pixel; and
segment vessels, the segmentation of the vessels comprising a decision by the imaging system, depending on the calculated corrected opacity for the respective pixel, whether the respective pixel belongs to a vessel.

15. The imaging system of claim 14, wherein the respective pixel belongs to a vessel when the corrected opacity of the pixel is greater than a predetermined opacity threshold value, and
wherein the greater the corrected opacity of the pixel is, the greater the maximum opacity of the pixel and the contrast agent arrival time of the pixel are.

16. An imaging system configured to create a selective vessel image within a volume section of an examination object, the creation of the selective vessel image comprising selectively representation or suppression, by the imaging system, of a vessel of the volume section in the selective vessel image in a manner dependent on at least one predetermined criterion, the imaging system comprising:
a processor configured to:
create a vessel image of the volume section, the creation of the vessel image comprising:
acquisition, by the imaging system, imaging data of the volume section within a predetermined time interval;
determination per pixel of the vessel image of a maximum opacity within the time interval on account of a contrast agent administered to the examination object; and
segmentation of vessels by the imaging system, the segmentation comprising a decision, depending on the maximum opacity of the pixel, whether the respective pixel belongs to a vessel;
determine a contrast agent arrival time per pixel of the vessel image; and
segment whether the respective vessel of the vessel image belongs to a vessel of the selective vessel image when an area of the vessel that is flowed through perpendicular to a flow direction is smaller than a predetermined maximum size threshold value and larger than a predetermined minimum size threshold value, and when the contrast agent arrival time of the pixels of the vessel is less than a predefined maximum threshold value and greater than a predefined minimum contrast agent arrival time threshold value.

17. The imaging system of claim 16, wherein the decision depends on the maximum opacity of the pixel and the contrast agent arrival time of the pixel.

18. In a non-transitory computer-readable storage medium storing instructions executable by a programmable control device of an imaging system to create a vessel image with a volume section of an examination object using an imaging system, the instructions comprising:
acquiring imaging data of the volume section within a predetermined time interval;
determining, per pixel of the vessel image, a maximum opacity within the predetermined time interval on account of a contrast agent administered to the examination object, wherein opacity represents a concentration of contrast agent per unit volume;
determining a contrast agent arrival time per pixel of the vessel image;
calculating a corrected opacity for each pixel of the vessel image based on the maximum opacity and the contrast agent arrival time for the respective pixel; and segmenting vessels, the segmenting comprising deciding, depending on the calculated corrected opacity for the respective pixel, the respective pixel belongs to a vessel.

\* \* \* \* \*